United States Patent
Matsuzawa (10) Patent No.: US 8,162,832 B2
(45) Date of Patent: Apr. 24, 2012

(54) MINOR AXIS MOTION TYPE ULTRASONIC PROBE

(75) Inventor: Itaru Matsuzawa, Saitama (JP)

(73) Assignee: Nihon Dempa Kogyo Co., Ltd., Tokyo (JP)

( * ) Notice: Subject to any disclaimer, the term of this patent is extended or adjusted under 35 U.S.C. 154(b) by 434 days.

(21) Appl. No.: 12/387,882

(22) Filed: May 8, 2009

(65) Prior Publication Data

US 2009/0299194 A1    Dec. 3, 2009

(30) Foreign Application Priority Data

May 28, 2008  (JP) .................... 2008-139317
Mar. 16, 2009  (JP) .................... 2009-063046

(51) Int. Cl.
*A61B 8/00*    (2006.01)
(52) U.S. Cl. ....... 600/437; 600/439; 600/441; 600/443; 600/407; 600/447
(58) Field of Classification Search ............ 600/437, 600/439, 441–443, 447, 407
See application file for complete search history.

(56) References Cited

U.S. PATENT DOCUMENTS

| | | | | |
|---|---|---|---|---|
| 5,050,128 | A * | 9/1991 | Saitoh et al. | 367/7 |
| 5,291,090 | A * | 3/1994 | Dias | 310/334 |
| 5,884,627 | A * | 3/1999 | Wakabayashi et al. | 600/447 |
| 2005/0090739 | A1 | 4/2005 | Tsubouchi et al. | 600/437 |
| 2005/0184624 | A1* | 8/2005 | Hasegawa et al. | 310/334 |
| 2008/0139945 | A1* | 6/2008 | Hu | 600/459 |

FOREIGN PATENT DOCUMENTS

| | | |
|---|---|---|
| JP | 57-23599 | 2/1982 |
| JP | 2007-267817 | 10/2007 |
| JP | 2008-80093 | 4/2008 |

OTHER PUBLICATIONS

"Fundamental Physics," vol. 1, Editor: Toshiro Kanehara, Publisher: Sadatsugu Abiko, Published: Feb. 1, 1971, p. 221 (Formula of Thin Lens).

* cited by examiner

*Primary Examiner* — Brian Casler
*Assistant Examiner* — Joel Lamprecht
(74) *Attorney, Agent, or Firm* — Scott D. Wofsy; Edwards Wildman Palmer LLP (57) ABSTRACT

The invention relates to a minor axis motion type ultrasonic probe with high sensitivity that suppresses propagation loss. The minor axis motion type ultrasonic probe of the invention comprises: a piezoelectric element group in which a plurality of piezoelectric elements are arranged in a line in a major axis direction of the piezoelectric element group; an acoustic lens that is provided on an ultrasonic wave transmitting/receiving surface side of the piezoelectric element group and that has a predetermined curvature in a minor axis direction of the piezoelectric element group; and a sealed container that houses the piezoelectric element group with the acoustic lens provided thereon and that is filled with a liquid serving as an ultrasonic wave medium, and the piezoelectric element group is moved in the minor axis direction and ultrasonic waves are transmitted and received to and from a living body, wherein the configuration is such that the acoustic lens is a concave lens formed from a material that has less propagation loss than a silicone resin and that has a greater acoustic velocity than a living body, and a relationship between acoustic velocity $c_1$ of the concave lens, acoustic velocity $c_2$ of the liquid, and acoustic velocity $c_3$ of the living body is expressed as $c_1 > c_3 > c_2$.

5 Claims, 6 Drawing Sheets

MINOR AXIS MOTION TYPE ULTRASONIC PROBE

TECHNICAL FIELD

The present invention relates to a minor axis motion type ultrasonic probe that rotates/oscillates or linearly reciprocates in the minor axis direction of a piezoelectric group, and in particular relates to an acoustic lens provided on an ultrasonic wave transmitting/receiving surface formed on a front surface of the piezoelectric element group.

PRIOR ART

In a minor axis motion type ultrasonic probe, a piezoelectric element group serving as an ultrasonic wave generating source, is mechanically scanned in the minor axis direction thereof, and is electronically scanned in the major axis direction thereof. Therefore, a minor axis motion type ultrasonic probe has recently drawn attention because compared for example to a matrix type that electronically scans in either the minor axis direction or the major axis direction, it makes electrical wiring easier and enables acquisition of a three dimensional image.

Figure 5A:
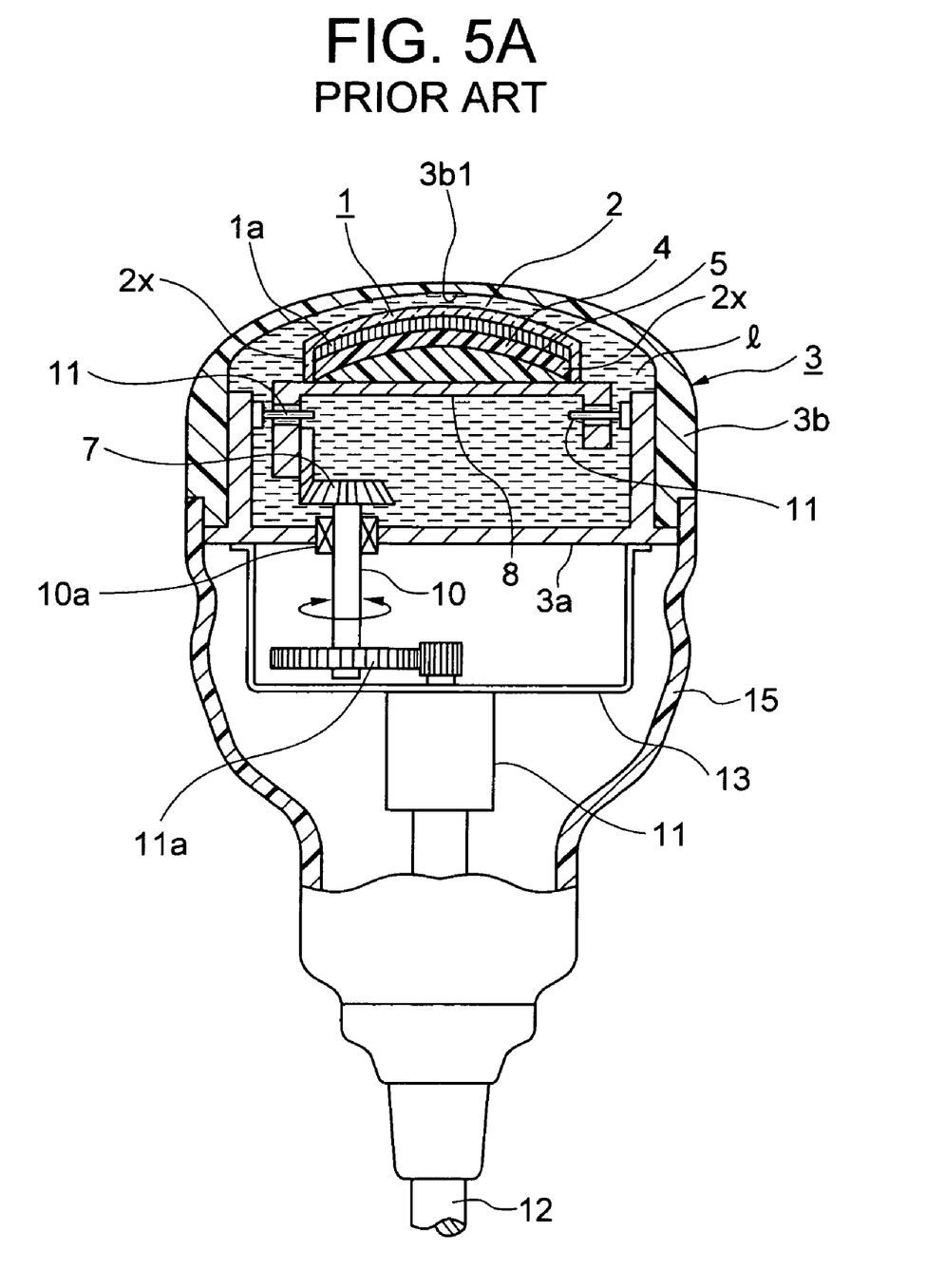
FIG. 5A is a major axis direction sectional view.
Figure 5B:
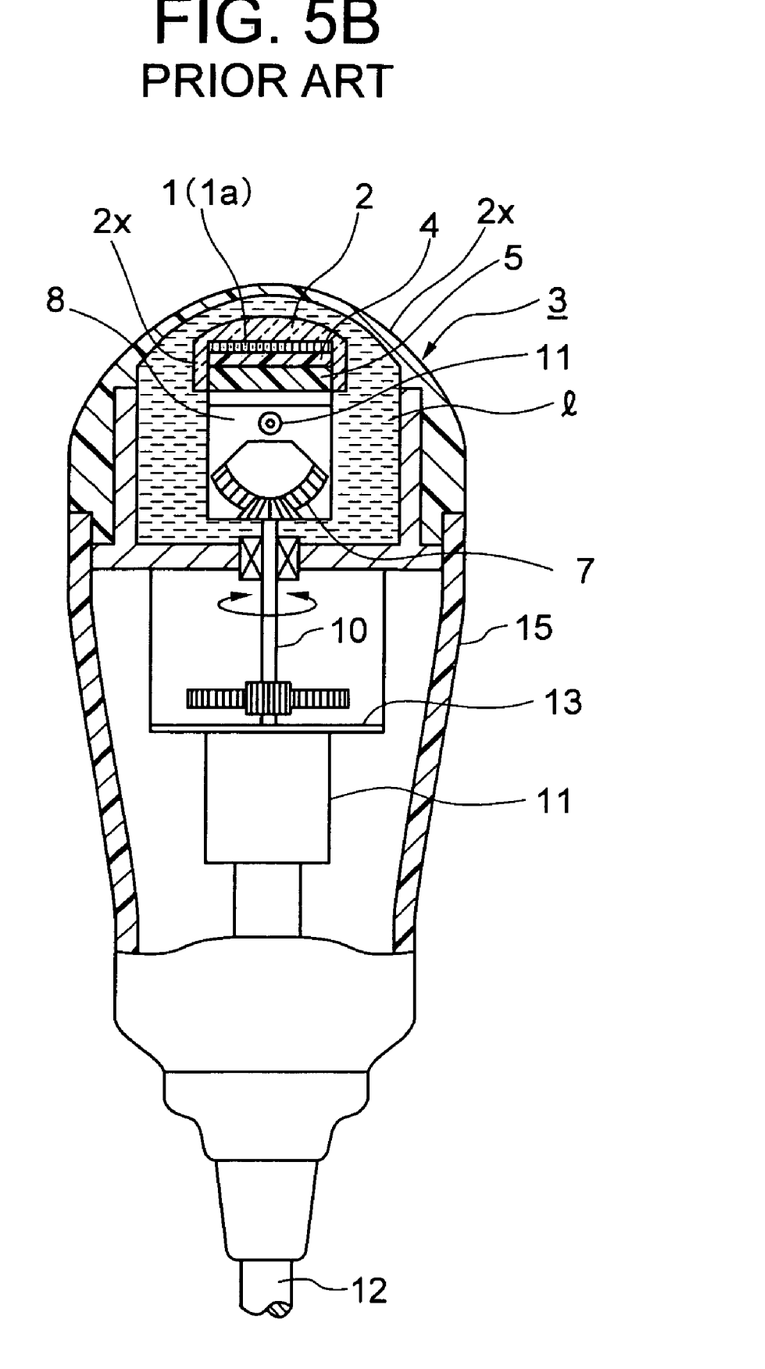
FIG. 5B is a minor axis direction sectional view.

FIG. 5 is a drawing for describing a conventional example of a minor axis motion type ultrasonic probe of a rotation/oscillation type, wherein FIG. 5A is a major axis direction sectional view thereof, and FIG. 5B is a minor axis direction sectional view thereof.

This ultrasonic probe is at least provided with a piezoelectric element group 1, an acoustic lens 2, and a sealed container 3. The piezoelectric element group 1 is formed with a plurality of piezoelectric elements 1a arranged in a line along the major axis direction which is their widthwise direction. Here these components are fixed on a backing member 4. The backing member 4 is fixed on a base 5 which is of an arc shape in the major axis direction, and consequently the piezoelectric element group 1 forms a convex shape in the major axis direction. On the piezoelectric element group 1 there is provided an acoustic matching layer (not shown in the drawing) for matching a living body (for example a female breast) with an acoustic impedance.

The acoustic lens 2 is provided on the acoustic matching layer which becomes the ultrasonic wave transmitting/receiving surface side of the piezoelectric element group 1, and is a convex lens having a curvature in the minor axis direction, which is the lengthwise direction of the piezoelectric elements. The acoustic lens 2 has a pair of leg sections 2x, and the leg sections 2x cover across the outside faces of the piezoelectric element group 1 and so forth. Here the acoustic lens 2 is formed from a silicone resin having an acoustic velocity lower than that of a living body.

Figure 6:
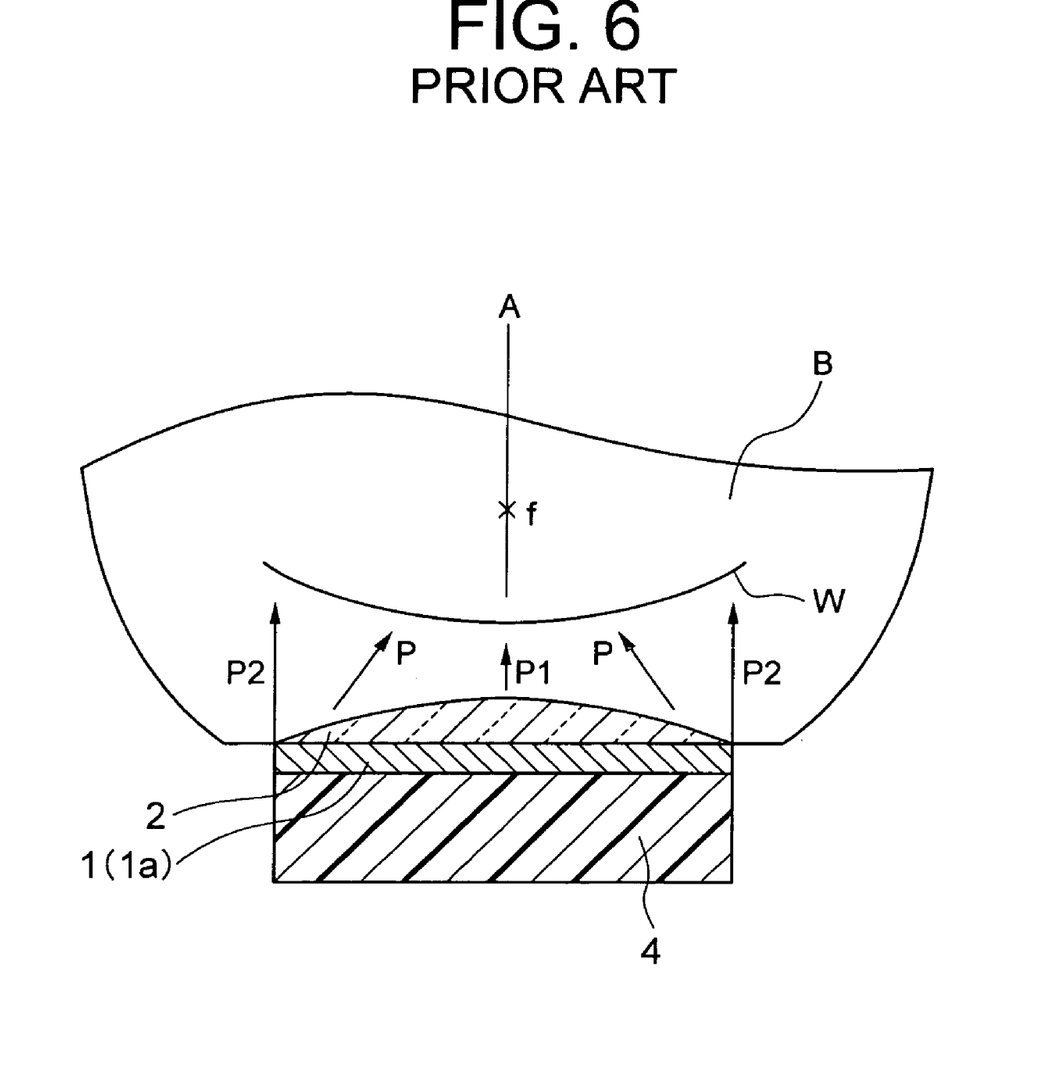
FIG. 6 is a partial sectional view for describing an effect of an acoustic lens used in the conventional example of the ultrasonic probe.

In the case of this conventional example, as shown in FIG. 6, propagation of an ultrasonic wave $P_2$ at both end sections of the acoustic lens 2 becomes faster than that of an ultrasonic wave $P_1$ at the center section where the thickness of the acoustic lens 2 is greatest. Therefore, as shown in FIG. 6, the wave front of the ultrasonic wave becomes a curved surface shown as a curved line W in which it is slowest at the center section of the acoustic lens 2. Consequently, ultrasonic waves P, as shown by solid lines, progress toward the center line A of the acoustic lens 2, and converge at a focal distance f shown by symbol x in accordance with the curvature of the acoustic lens 2. Consequently the ultrasonic wave propagation efficiency with respect to a detection target section (affected section) of a living body B is increased.

As shown in FIG. 5A and FIG. 5B, the sealed container 3 of the piezoelectric element group 1 and the acoustic lens 2 comprises a container main body (inner case) 3a and a cover 3b covering this container main body 3a, both having a sectionally concave shape. To the container main body 3a, there is attached a fixed base 8 that is rotated/oscillated in the minor axis direction by a motor 11, a bevel gear mechanism 7, and so forth. On the fixed base 8 there is previously fixed the base 5 having the piezoelectric element group 1 fixed thereon. Furthermore, the acoustic lens 2 provided on the ultrasonic wave transmitting/receiving surface side of the piezoelectric element group 1 faces an inner wall surface $3b_1$ of the cover 3b, and ultrasonic waves from the cover 3b are transmitted and received to and from a living body B.

The inner space of the sealed container 3 is filled, from an injection hole (not shown in the drawing) of the sealed container 3, with a liquid l such as polypropylene glycol that serves as an ultrasonic wave medium for preventing attenuation of ultrasonic waves from the piezoelectric element group 1. In a case where the sealed container 3 is not filled with the liquid l and air is present in between the inner wall surface $3b_1$ of the cover 3b and the surface of the piezoelectric element group 1, attenuation of ultrasonic waves is significant and propagation efficiency is deteriorated, so that normal transmission and reception of ultrasonic waves to and from a living body cannot be expected.

In FIG. 5A and FIG. 5B, reference symbol 10 denotes a drive shaft of a bevel gear 7, reference symbol 10a denotes a bearing thereof, and reference symbol 11 denotes a pin that allows free rotation of the fixed base 8.

The drive shaft 10 of the bevel gear 7 is housed within a housing 15 fitted to an edge section of the cover 3b of the sealed container 3, and is rotated, via a gear train 11a bearing-supported on a bracket 13, by the motor 11 connected to a conductive cable 12.

(Refer to: [Patent Document 1] Japanese Unexamined Patent Publication No. 2007-267817; [Patent Document 2] Japanese Unexamined Patent Publication No. 2008-80093; [Patent Document 3] Japanese Unexamined Utility Model Publication No. Sho 57-23599; and [Non-Patent Document 1] "Fundamental Physics, Volume 1, Editor: Toshiro Kanehara, Publisher: Sadatsugu Abiko, Published: Feb. 1, 1971, p. 221 (Formula of Thin Lens)")

PROBLEMS IN THE CONVENTIONAL TECHNIQUE

However, in the conventional ultrasonic probe having the above configuration, since the acoustic lens 2 (convex lens) is formed from a silicone resin (rubber), the propagation loss of ultrasonic waves is significant. In this case, the closer the section to be diagnosed is to the surface of the living body B and the shorter the focal distance f of the ultrasonic wave, the smaller the radius of curvature of the acoustic lens 2.

Consequently, the thickness of the acoustic lens 2 in the center section becomes greater, and hence the propagation loss becomes more significant. Therefore, there has been a problem in that as the propagation loss increases the sensitivity of the ultrasonic probe is reduced.

Incidentally, if the acoustic velocity of the living body B (the velocity at which an acoustic wave travels through a living body; the same applies hereunder) serving as an ultrasonic wave medium is $c_3$ (1500 m/s), the acoustic velocity of the acoustic lens 2 formed from a silicone resin is $c_1$ (1000 m/s), and the focal distance is f, the radius of curvature r of the acoustic lens 2 can be expressed by the following expression (A). Here, n is the refractive index of the acoustic lens where the living body B is taken as a reference, and $n=c_1/c_3$. If the radius of curvature r in expression (A) is negative, it is a convex lens, and if positive, it is a concave lens.

$$r = f\{1 - (c_3/c_1)\} \quad\quad (A)$$
$$= f\{(n-1)/n\}$$

As can be seen from expression (A), the shorter the focal distance f, the smaller the radius of curvature of the acoustic lens 2. Normally, in a case where a deep section from the surface of a living body B is to be diagnosed (where the focal distance f is long), an ultrasonic wave in a low frequency zone, for example 3.5 MHz, is applied, and in a case where the vicinity of the body surface is to be diagnosed (where the focal distance f is short), an ultrasonic wave in a high frequency zone, for example 10 MHz, is applied. The acoustic velocity $c_2$ (1370 m/s) of the liquid l serving as an ultrasonic wave medium also has an influence on this, however it is normally processed as being equivalent to the acoustic velocity $c_3$ of the living body.

Object of the Invention

An object of the present invention is to provide a minor axis motion type ultrasonic probe in which propagation loss is suppressed and sensitivity is increased.

DISCLOSURE OF THE INVENTION

Points for Attention

In the present invention, firstly, the inventor of the present invention focused on a point that a resin with an acoustic velocity greater than that of a living body but with a smaller propagation loss than a silicone resin, is used for the acoustic lens, and this is applied as a concave lens.

Secondly, the present inventor focused on a point that if the acoustic velocity of a liquid filled within a sealed container to serve as an ultrasonic wave medium is less than the acoustic velocity of a living body, the acoustic velocity difference between the concave lens and the liquid is greater than the acoustic velocity difference between the concave lens and the living body, and the thickness of the concave lens can thus be made thinner.

Means for Solving the Problems

The present invention is a minor axis motion type ultrasonic probe that comprises: a piezoelectric element group in which a plurality of piezoelectric elements are arranged in a line in a major axis direction, which is a widthwise direction of the piezoelectric elements; an acoustic lens that is provided on an ultrasonic wave transmitting/receiving surface side of the piezoelectric element group and that has a curvature in a minor axis direction, which is a lengthwise direction of the piezoelectric elements; and a sealed container that houses the piezoelectric element group with the acoustic lens provided thereon and that is filled with a liquid serving as an ultrasonic wave medium, and the piezoelectric element group is moved in the minor axis direction and ultrasonic waves are transmitted and received to and from a living body, wherein the configuration is such that the acoustic lens is a concave lens formed from a material that has less propagation loss than a silicone resin and that has a greater acoustic velocity than a living body, and a relationship between acoustic velocity $c_1$ of the concave lens, acoustic velocity $c_2$ of the liquid, and acoustic velocity $c_3$ of the living body is expressed as $c_1 > c_3 > c_2$.

Effect of the Invention

According to such a configuration, the relationship is expressed as $c_1 > c_3 > c_2$ where the acoustic velocities of a concave lens, a liquid l, and a living body B are respectively taken as $c_1$, $c_2$, and $c_3$. Therefore, the acoustic velocity difference between the concave lens and the liquid ($c_1-c_2$) is greater than the acoustic velocity difference between the concave lens and the living body B ($c_1-c_3$). Here, if the radius of curvature r of the concave lens is the same, the focal distance f becomes shorter as the acoustic velocity difference between the concave lens and the liquid becomes greater. Conversely, if the focal distance f is the same distance, the radius of curvature of the lens becomes greater as the acoustic velocity difference is greater. Consequently, it is possible to make the thickness of the concave lens with consideration of a liquid having an acoustic velocity lower than that of a living body, thinner than the thickness of a concave lens with no consideration of a liquid.

Moreover, the concave lens that serves as an acoustic lens is formed from a resin having a propagation loss less than that in a silicone resin. Consequently, even if the thickness of the concave lens where $c_1 > c_3 > c_2$, becomes greater than that of a conventional convex lens formed from a silicone resin, it is possible to suppress propagation loss of ultrasonic waves and improve the sensitivity of the probe.

Embodiment

Furthermore, in the present invention, a radius of curvature r of the concave lens with respect to a focal distance f is determined as $r=\{(c_1-c_2)/c_1 \cdot c_2\} \cdot c_3 \cdot f$. As a result it is possible to easily determine the radius of curvature of the concave lens corresponding to the focal distance f. As described later in the embodiment, the above expression is derived based on expression (3) in "Fundamental Physics, Volume 1, Editor: Toshiro Kanehara, Publisher: Sadatsugu Abiko, Published: Feb. 1, 1971, p. 221 (Formula of Thin Lens)".

Moreover, in the present invention, the acoustic lens is formed from a methyl pentene resin, and the liquid is polypropylene glycol. As a result, the acoustic velocity $c_1$ of the methyl pentene resin of the acoustic lens is 2050 m/s, and also the acoustic lens is a concave lens 2a with an acoustic velocity greater than the acoustic velocity $c_3$ of the living body B (1500 m/s). Thereby, it can be employed as an acoustic lens. Furthermore, as described later, since the amount of attenuation per unit length of the methyl pentane resin is approximately 0.448 dB/mm/MHz, the amount of attenuation is smaller than that of the silicone resin at approximately 1.0 dB/mm/MHz.

The polypropylene glycol used as the liquid has an acoustic velocity $c_2$ of 1370 m/s, which is lower than the acoustic velocity $c_3$ of the living body. Consequently, the acoustic velocity difference ($c_1-c_2$) between the concave lens (acoustic velocity $c_1$) and the liquid can be made greater than the acoustic velocity difference ($c_1-c_3$) between the concave lens and the living body, and hence the configuration of $c_1 > c_3 > c_2$ can be realized. The acoustic velocity of the methyl pentene resin of the acoustic lens is also high, and hence its propagation loss for ultrasonic waves is also small.

Moreover, in the ultrasonic probe of the present invention, the piezoelectric element group rotates/oscillates in an arc shape in the minor axis direction or reciprocates linearly in the minor axis direction. As a result, the function of the minor axis motion type ultrasonic probe can be sufficiently realized.

BRIEF DESCRIPTION OF THE DRAWINGS

FIG. 4 is a drawing for describing another embodiment of the present invention, wherein

FIG. 5 is a drawing for describing a conventional example of a minor axis motion type ultrasonic probe of a rotation/oscillation type, wherein

DETAILED DESCRIPTION OF THE PREFERRED EMBODIMENTS

Figure 1:
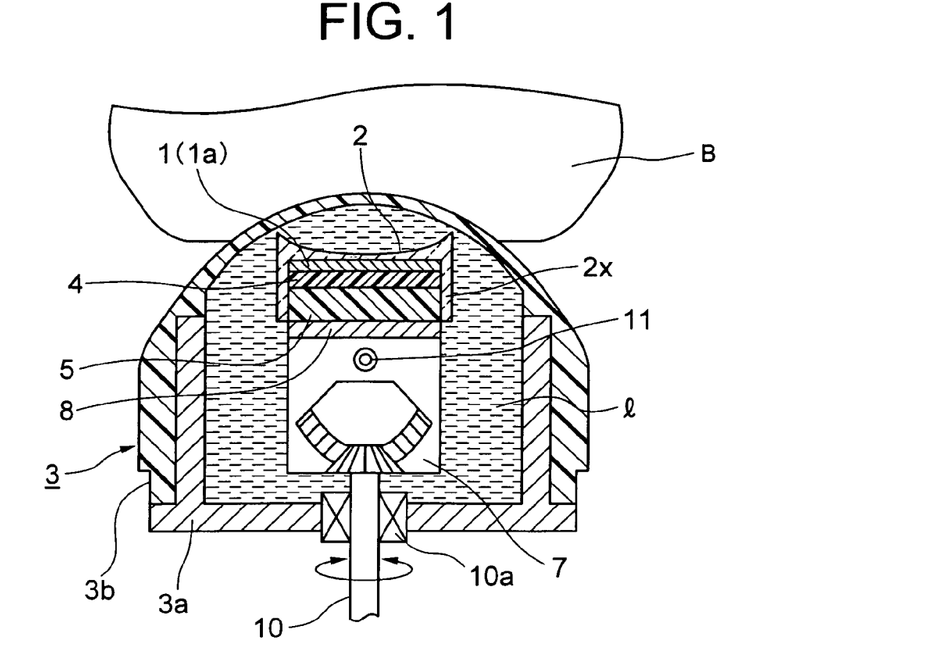
FIG. 1 is a minor axis direction sectional view for describing an embodiment of an ultrasonic probe of the present invention. Here, a housing that houses a motor and so forth is omitted from the drawing.

FIG. 1 is a minor axis direction sectional view for describing an embodiment of an ultrasonic probe of the present invention.

The ultrasonic probe of the present invention is configured such that a piezoelectric element group 1 arranged in the major axis direction and with an acoustic lens 2 having a predetermined curvature in the minor axis direction provided on an ultrasonic wave transmitting/receiving surface side, is housed within a sealed container 3.

The inside of the sealed container 3 is filled with a liquid 1 that serves as an ultrasonic wave medium, and the piezoelectric element group 1 is fixed on a fixed base 8 that rotates/oscillates within a container main body 3a, so as to rotate/oscillate in the minor axis direction of the ultrasonic probe. Furthermore, ultrasonic waves from a cover 3b side are transmitted/received to/from a living body B.

Moreover, in this embodiment, the acoustic lens 2 is made as a concave lens 2a having a pair of leg sections 2x, and the concave surface thereof is arranged so as to face the living body side (cover side). The concave lens 2a is formed from a methyl pentene resin (commonly known as TPX resin), and the acoustic velocity $c_1$ thereof is 2050 m/s, which is greater than the acoustic velocity $c_3$ (1500 m/s) within the living body B. Furthermore the liquid 1 filled within the sealed container 3 and serving as an ultrasonic wave medium is made from polypropylene glycol, and the acoustic velocity $c_2$ thereof is 1370 m/s, which is lower than the acoustic velocity $c_3$ of the living body B.

Here, the acoustic velocity of the acoustic lens, the acoustic velocity of the liquid, and the acoustic velocity of the living body respectively refer to the acoustic velocity for when ultrasonic waves travel through these objects.

That is to say, in the present invention, the relationship between the respective acoustic velocities $c_1$, $c_2$, and $c_3$ of the acoustic lens 2 (concave lens 2a), the liquid 1, and the living body B, is expressed as $c_1 > c_3 > c_2$. As a result, the acoustic velocity $c_1$ of the concave lens 2a is greater than the acoustic velocities $c_2$ and $c_3$ of the liquid 1 and the living body B. Therefore, the degree of progress of ultrasonic waves traveling through both of the end sections of the concave lens 2a where the thickness is thick and reaching the living body B, becomes faster than that of ultrasonic waves traveling through the center section where the thickness is thin. Consequently, as with a convex lens, this has a focal distance f corresponding to the curvature of the concave lens 2a, and the ultrasonic waves converge on the center line within the living body B.

Figure 2:
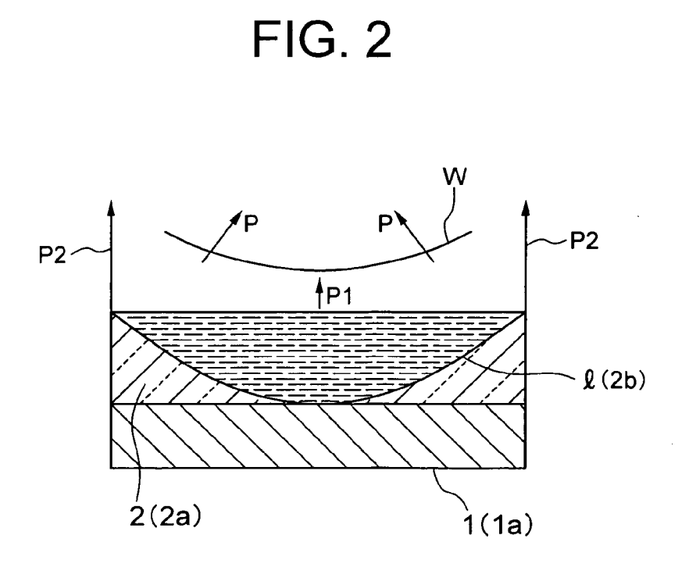
FIG. 2 is schematic partial minor axis direction sectional view for describing an effect of an embodiment of the ultrasonic probe of the present invention.

In this case, as schematically shown in FIG. 2 for example, the liquid 1 filled within the concave surface of the concave lens 2a forms a convex lens 2b, and the concave lens 2a and the convex lens 2b form a laminated lens with a parallel plane between both principal surfaces. In this case, the inner circumferential radius of curvature r of the concave lens 2a is equal to the outer circumferential radius of curvature r of the convex lens 2b. In FIG. 2, for convenience, the center of the convex lens is made a pointedly exposed parallel plane.

Therefore, as shown in FIG. 2, firstly, an ultrasonic wave P transmitted from the piezoelectric element group 1 housed within the sealed container 3 is such that due to the concave lens 2a (acoustic velocity $c_1$) and the liquid 1 with a velocity $c_2$ lower than this, progress of an ultrasonic wave $P_2$ at both of the end sections of the concave lens 2a (ultrasonic wave $P_2$) is fast, and progress of an ultrasonic wave $P_1$ in the center section of the concave lens 2a is slow. As a result, the ultrasonic wave $P_2$ in both of the end sections progresses faster than the ultrasonic wave $P_1$ in the center section, until it reaches the opening end surface (horizontal surface) of the concave lens 2a with the liquid 1 filled therein.

Next, having passed the opening end surface of the concave lens 2a, the acoustic velocities of the ultrasonic wave $P_2$ in both of the end sections of the concave lens and the ultrasonic wave $P_1$ in the center section both become the acoustic velocity $c_2$ in the liquid 1, and they progress at the same velocity while maintaining a progress distance difference of the ultrasonic wave. Finally, the ultrasonic wave P, while maintaining the progress distance difference, progresses from the surface of the cover 3b shown in FIG. 1 through the inside of the living body B at the same velocity as the acoustic velocity $c_3$. Then the ultrasonic waves converge within the living body B at the focal distance f determined based on the radius of curvature r of the concave lens 2a.

According to such a configuration of the present invention, the acoustic lens 2 (concave lens 2a) is formed from a resin with attenuation of ultrasonic waves that is smaller than that for a silicone resin. Consequently, even if the thickness of the concave lens 2a becomes greater than a convex lens that uses of a conventional silicone resin, it is possible to basically reduce the amount of attenuation of ultrasonic waves.

Moreover, as described above, an empty space (cavity) of the concave lens 2a filled with the liquid 1, that is, the center section of the laminated lens comprising the concave lens 2a and the convex lens 2b becomes a section with a maximum thickness of the convex lens 2b formed from the liquid 1 with an acoustic velocity that is lower than that of the concave lens 2a, and, consequently, the progress of ultrasonic waves becomes slower. Furthermore, as shown in FIG. 2, both of the end sections of the laminated lens become the maximum thickness section of the concave lens 2a in which the acoustic velocity is higher than that in the liquid 1 (convex lens). Therefore the progress of ultrasonic waves becomes faster.

Consequently, with the laminated lens with consideration of the convex lens 2b formed from the liquid 1, the progress distance difference between the ultrasonic waves $P_1$ and $P_2$ becomes significant between the center section and both of the end sections of the convex lens 2b. As a result, compared to the case of only the concave lens 2a without consideration of the liquid l, it is possible to make the thickness of the laminated lens (2a, 2b) having a parallel plane with consideration of the liquid l thinner, in other words, it is possible to make the thickness of the concave lens 2a, with the inside of the concave surface of the concave lens 2a filled with the liquid l, thinner.

That is to say, as disclosed in the above Effect of the Invention section of the present specification, in the present invention, the relationship between the acoustic velocities $c_1$, $c_2$, and $c_3$ of the concave lens 2a, the liquid l, and the living body B is defined as $c_1 > c_3 > c_2$. Therefore, the acoustic velocity difference ($c_1 - c_2$) between the concave lens 2a and the liquid l is greater than the acoustic velocity difference ($c_1 - c_3$) between the concave lens 2a and the living body B. In this case, if the radius of curvature r of the concave lens 2a is same, the focal distance f becomes shorter as the acoustic velocity difference becomes greater.

In other words, if the focal distance f is the same distance, the radius of curvature of the concave lens 2a becomes greater as the acoustic velocity difference becomes greater. Consequently, it is possible to make the thickness of the concave lens 2a with consideration of the liquid l, thinner than that of the concave lens 2a without consideration of the liquid l. As a result, it is possible to further suppress propagation loss (amount of attenuation) of ultrasonic waves traveling through the acoustic lens 2 (concave lens 2a) while improving the sensitivity of the ultrasonic probe.

(Curvature r of the Acoustic Lens 2 and its Criterion)

Figure 3:
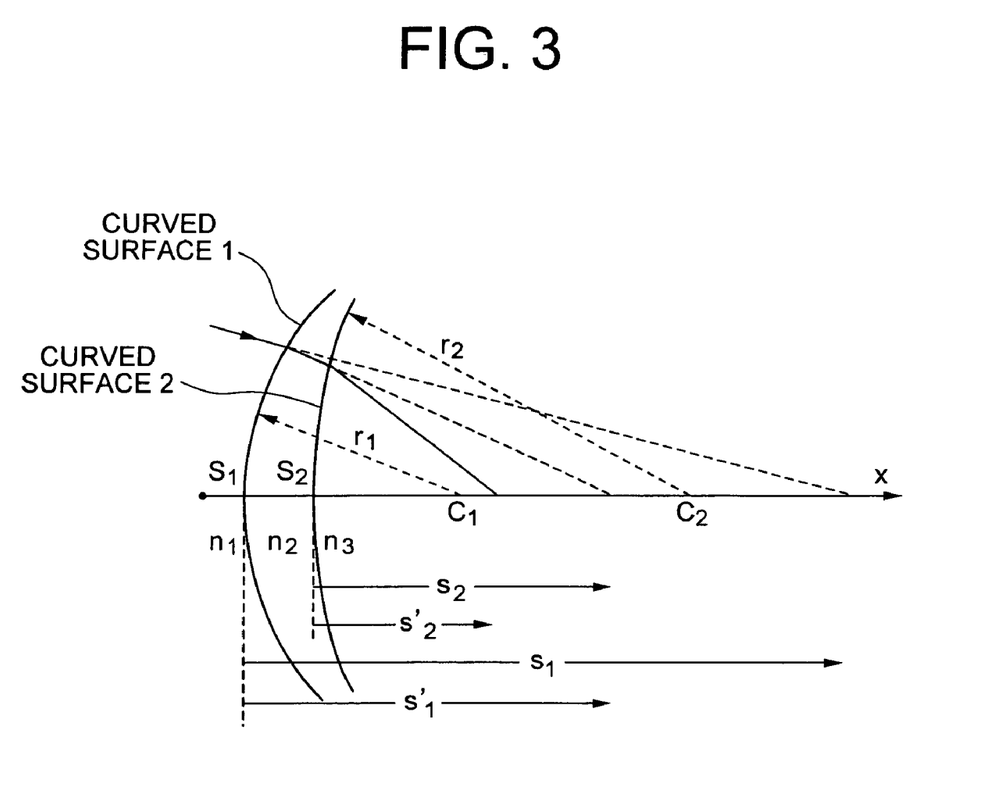
FIG. 3 is a conceptual drawing for describing an effect of a thin lens that lead to the embodiment of the present invention.

Incidentally, a curvature $r_1$ of the concave lens 2a shown in FIG. 3, based on a predefined focal distance f, is determined by the following expression (B), where the acoustic velocities $c_1$, $c_2$, and $c_3$ are taken as the velocities of the concave lens 2a, the liquid l serving as the convex lens 2b, and the living body B. In the conventional example, the acoustic velocity $c_2$ of the liquid l was not considered as equivalent to that of the living body B.

$$r = \{(c_1 - c_2)/(c_1 \cdot c_2)\} \cdot c_3 \cdot f \quad (B)$$

The above expression (B) is derived as described below from image formation expressions (1) and (2) for a thin lens shown in the aforementioned Non-Patent Document ("Fundamental Physics"). That is to say, in the aforementioned Patent Document 1, as shown in FIG. 3 (the same as FIG. 11. 4-11 of the aforementioned Non-Patent Document 1), in the case where media with refractive indexes $n_1$, $n_2$, and $n_3$ are sequentially brought into contact with curved surfaces 1 and 2 having radii of curvatures $r_1$ and $r_2$, the image formation expressions of the respective curved surfaces 1 and 2 are defined as the following expressions (1) and (2).

$$n_2/s_1' - n_1/s_1 = (n_2 - n_1)/r_1 \quad (1)$$

$$n_3/s_2' - n_2/s_2 = (n_3 - n_2)/r_2 \quad (2)$$

Here, intersecting points between the main axis shown with the coordinate axis x and the respective curved surface are taken as $S_1$ and $S_2$, and the distance between $S_1$ and $S_2$ ($S_1 S_2$) is sufficiently short. Here, $s_1$ and $s_1'$ are distances from the intersecting point $S_1$, and $s_2$ and $s_2'$ are distances from the intersecting point $S_2$. Moreover, in FIG. 3, $C_1$ denotes the center of the curved surface 1 with the radius of curvature $r_1$, and $C_2$ denotes the center of the curved surface 2 with the radius of curvature $r_2$, and for example, a case where $r_1 < r_2$ is shown. In the expressions (1) and (2), $s_1'$ and $s_2'$ are focal distances f of incident light (solid lines) associated with the respective curved surfaces 1 and 2.

Here, $s_2$ shown in FIG. 3 is $s_2 = s_1' S_1 S_2$. However, the distance between $S_1$ and $S_2$ may be ignored assuming a thin lens, and hence $s_2 = s_1'$ results. Consequently, if $s_2$ is removed from the above expressions (1) and (2), the following expression (3) results.

$$(n_3/s_2') - (n_1/s_1) = (n_2-1)(1/r_1 - 1/r_2) + \{(n_3-1)/r_2 - (n_1-1)/r_1\} \quad (3)$$

The items above are those disclosed in the aforementioned Non-Patent Document 1. However, here in the present invention, the case is assumed where the curved surface 2 (radius of curvature $r_2$) is a flat surface, that is to say, the radius of curvature is infinity ($\infty$).

In this case, since the radius of curvature r is infinity ($\infty$), the above expression (3) becomes the following expression (4). Then, if $s_1$ is $-\infty$, in other words, if an incident wave is a wave from an infinity-distanced point source (that is, a parallel wave), the following expression (5) results.

$$(n_3/s_2') - (n_1/s_1) = (n_2 - n_1)/r_1 \quad (4)$$

$$(n_3/s_2') = (n_2 - n_1)/r_1 \quad (5)$$

Consequently, from expression (5), there is derived a relationship between the focal distance f, that is $s_2'$, the media $n_1$, $n_2$, and $n_3$, and the radius of curvature $r_1$ of the curved surface 1 for when the curved surface 2 shown in FIG. 3 is a flat surface (radius of curvature r is $\infty$) and the incident light is a parallel wave. For example, if the expression (5) is modified to find the radius of curvature $r_1$ of the curved surface 1, the following expression (6) results.

$$r_1 = \{(n_2 - n_1)/n_3\} s_2' \quad (6)$$

Here, the above media with refractive indices $n_1$, $n_2$, and $n_3$ are taken as the concave lens 2a, the convex lens 2b formed from the liquid l, and the living body B in the present embodiment. In this case, if the acoustic velocity $c_3$ (1500 m/s) of the living body B is taken as a reference, the refractive indexes $n_1$, $n_2$ and $n_3$ of the concave lens 2a (acoustic velocity $c_1$), the convex lens 2b (acoustic velocity $c_2$), and the living body B, become $c_3/c_1$, $c_3/c_2$, $c_3/c_3 (=1)$.

Consequently, the above expression (6) becomes the following expression (7) (the same as the above expression (B)). However, $s_2' = f$. As a result, from the focal distance $f (=s_2')$ in the living body B and the acoustic velocities of the concave lens 2a and the convex lens 2b, there can be found the radius of curvature $r_1$ of the convex lens 2b (concave lens 2a).

$$r_1 = \{(c_3/c_2) - (c_3/c_1)\} s_2'$$
$$= \{(c_1 - c_2)/(c_1 \cdot c_2)\} \cdot c_3 \cdot f (7) [ = (B)]$$

(Thicknesses of the Acoustic Lenses)

For example, when the ultrasonic wave frequency is 7.5 MHz, and the length L in the minor axis direction of the piezoelectric element 1 is 6 mm and the focal distance f is 20 mm, then in the case of not considering the presence of the liquid l as the convex lens of the conventional example formed from a silicone resin, the radius of curvature r is calculated as 9.98 mm from the above expression (A), and the maximum thickness section at the center section of the convex lens becomes 0.462 mm.

Moreover, under the same condition of the ultrasonic wave frequency and the length L in the minor axis direction of the ultrasonic probe, in the case of the acoustic lens 2 with no consideration of the presence of the liquid l as the concave lens 2a formed from a methyl pentene resin, the radius of curvature r is similarly calculated as 5.36 mm from the expression (A), and the maximum thickness section at both of the end sections of the concave lens 2a is 0.92 mm. For these values of the maximum thickness sections, the radius of curvature r can be found from the expression (A), and therefore, the maximum thickness section of the convex lens can be calculated as long as the length L in the minor axis direction is given.

Furthermore, under the same condition, with the concave lens 2a formed from a methyl pentene resin, in the case of the acoustic lens 2 (the laminated lens comprising the concave lens 2a and the convex lens 2b) with consideration of the presence of the liquid 1 in the present invention, the radius of curvature is 7.26 mm based on the expression (B) according to the present invention, and the maximum thickness section at both of the end sections of the concave lens 2a becomes 0.66 mm from the length L.

From these results, the size of the concave lens 2a formed from a methyl pentene resin becomes greater than that of the convex lens of the conventional example even without considering the presence of the liquid 1. However, on the other hand, the thickness of the concave lens 2a (laminated lens) with consideration of the presence of the liquid 1 can be made smaller by approximately 30 percent than that of the concave lens 2a with no consideration of the presence of the liquid 1.

(Amounts of Attenuation of the Acoustic Lenses)

Here, an amount of attenuation A (dB) of ultrasonic waves traveling through the acoustic lens 2 is proportional to the ultrasonic wave frequency f (MHz), and is found as $A=\alpha \cdot t \cdot f$ (dB). Here, $\alpha$ is an amount of attenuation per unit length (1 mm), and t is a thickness of the maximum thickness section of the aforementioned concave lens. Moreover, the amount of attenuation per unit length of the conventional convex lens formed from a silicone resin is approximately 1.0 dB/mm/MHz, and the amount of attenuation per unit length of the concave lens 2a of the present invention formed from a methyl pentene resin is approximately 0.448 dB/mm/MHz.

From these results, if the ultrasonic wave frequency f is 7.5 MHz as mentioned above, an amount of attenuation A1 in the convex lens using the silicone resin is 3.465 dB (1×0.462× 7.5). On the other hand, an amount of attenuation A2 in the concave lens 2a using the methyl pentene resin that takes no consideration of the presence of the liquid 1 is 3.091 dB (0.448×0.92×7.5), and an amount of attenuation A3 in the concave lens 2a (laminated lens comprising 2a and 2b) of the present invention with consideration of the presence of the liquid 1 is 2.21 dB (0.448×0.66×7.5).

Consequently, the thickness of the concave lens 2a using the methyl pentene resin is greater than that of the convex lens using the silicone resin. However, when considering the amount of attenuation a per unit length, regardless of the presence of the liquid 1 within the concave surface of the concave lens 2a, the amounts of attenuation A2 and A3 of the concave lens 2a using the methyl pentene resin are smaller than the amount of attenuation A1 of the convex lens using the silicone resin.

Furthermore, the amount of attenuation A3 (2.21 dB) of the concave lens 2a (laminated lens) with consideration of the presence of the liquid 1 within the concave surface of the concave lens of the present invention becomes smaller by approximately 30 percent than the amount of attenuation A2 (3.091 [dB]) of the concave lens 2a with no consideration of the liquid 1 within the concave surface of the concave lens 2. Moreover the amount of attenuation A2 becomes smaller by approximately 40 percent than the amount of attenuation A1 (3.465 dB) of the conventional convex lens using the silicone resin. From these results, in the embodiment of the present invention, it is possible to obtain an ultrasonic probe with high sensitivity that suppresses propagation loss (amount of attenuation) in the acoustic lens 2 (concave lens 2a).

Another Embodiment

Figure 4A:
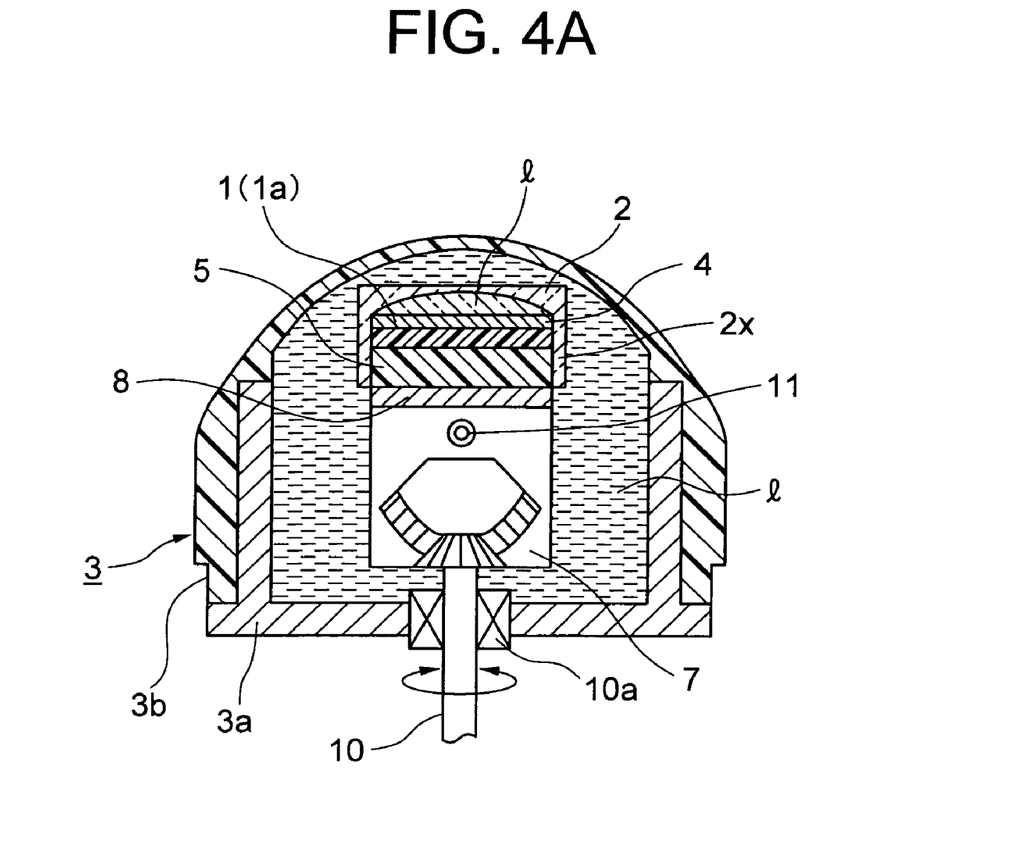
FIG. 4A is a minor axis direction sectional view of an ultrasonic probe and FIG. 4B is a perspective view of an acoustic lens.
Figure 4B:
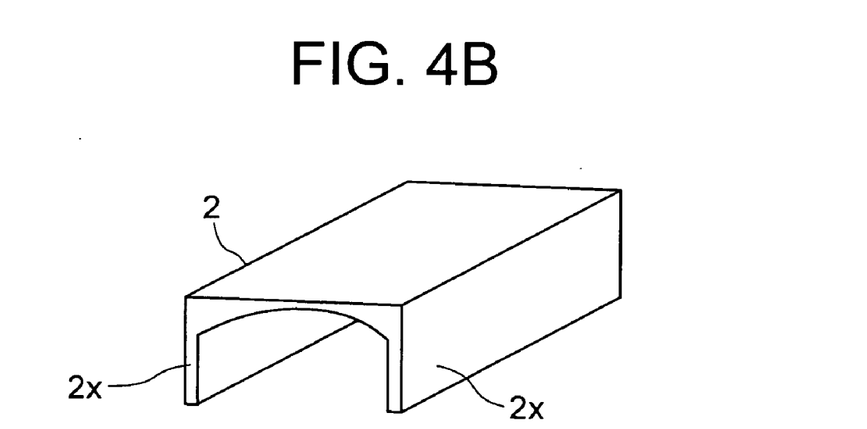

In the above embodiment, the concave surface of the concave lens 2a is arranged so as to face a living body. However, even if the concave surface of the concave lens 2a is arranged so as to face the piezoelectric element group 1 side as shown in FIG. 4A for example, a similar effect can be achieved. In this case, as shown in FIG. 4B, for example both end sides in the major axis direction of the acoustic lens 2 having a pair of the leg sections 2x are opened, and the inside of the concavity of the acoustic lens 2 is filled with the liquid 1, to thereby form a laminated lens.

Moreover, in the above embodiment, the piezoelectric element group 1 is arranged to rotate/oscillate in the minor axis direction thereof. However, as shown in Patent Document 2 for example, the piezoelectric element group 1 may be linearly reciprocated in the minor axis direction thereof. Essentially, the present invention may be applied to an ultrasonic probe in which a piezoelectric element group 1 is housed within a liquid 1, and ultrasonic waves from an acoustic lens are transmitted/received from/to a living body.

What is claimed is:

1. A minor axis motion type ultrasonic probe comprising:
a piezoelectric element group in which a plurality of piezoelectric elements are arranged in a line in a major axis direction of the piezoelectric element group;
an acoustic lens that is provided on an ultrasonic wave transmitting/receiving surface side of said piezoelectric element group and that has a curvature in a minor axis direction of said piezoelectric element group; and
a sealed container that houses said piezoelectric element group with said acoustic lens provided thereon and that is filled with a liquid serving as an ultrasonic wave medium, and said piezoelectric element group is moved in said minor axis direction and ultrasonic waves are transmitted and received to and from a living body,
wherein said acoustic lens is a concave lens formed from a material that has less propagation loss of ultrasonic waves than a silicone resin and that has a greater acoustic velocity than a living body, and a relationship between acoustic velocity $c_1$ of said concave lens, acoustic velocity $c_2$ of said liquid, and acoustic velocity $c_3$ of said living body is expressed as $c_1 > c_3 > c_2$.

2. A minor axis motion type ultrasonic probe according to claim 1, wherein a radius of curvature r of said concave lens with respect to a focal length f is determined as $r=\{(c_1-c_2)/c_1 * c_2\} * c_3 * f$.

3. A minor axis motion type ultrasonic probe according to claim 1, wherein said acoustic lens is formed from a methyl pentene resin, and said liquid serving as an ultrasonic wave medium comprises polypropylene glycol.

4. A minor axis motion type ultrasonic probe according to claim 1, wherein said piezoelectric element group rotates/oscillates in an arc shape in the minor axis direction of said piezoelectric element group.

5. A minor axis motion type ultrasonic probe according to claim 1, wherein said piezoelectric element group reciprocates linearly in the minor axis direction of said piezoelectric element group.

* * * * *